(12) United States Patent
Rassman et al.

(10) Patent No.: US 9,259,236 B1
(45) Date of Patent: *Feb. 16, 2016

(54) HAIR HARVESTING DEVICE AND METHOD WITH LOCALIZED SUBSURFACE DERMAL FLUID INSERTION

(71) Applicants: William Rassman, Los Angeles, CA (US); Jae Pak, Los Angeles, CA (US)

(72) Inventors: William Rassman, Los Angeles, CA (US); Jae Pak, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/758,808

(22) Filed: Feb. 4, 2013

Related U.S. Application Data

(63) Continuation of application No. 12/233,514, filed on Sep. 18, 2008, now Pat. No. 8,366,723.

(51) Int. Cl.
- *A61B 17/50* (2006.01)
- *A61B 17/3205* (2006.01)
- *A61B 17/32* (2006.01)
- *A61B 17/00* (2006.01)

(52) U.S. Cl.
CPC . *A61B 17/32053* (2013.01); *A61B 2017/00752* (2013.01); *A61B 2017/320064* (2013.01)

(58) Field of Classification Search
CPC ............... A61B 2017/00752; A61B 10/0233; A61B 10/0266; A61B 10/0283; A61B 17/3203; A61B 17/32053; A61B 17/32093; A61B 17/34; A61B 17/3401
USPC .......................................... 606/133; 604/272
See application file for complete search history.

(56) References Cited

U.S. PATENT DOCUMENTS

| | | | | |
|---|---|---|---|---|
| 6,572,625 | B1 * | 6/2003 | Rassman | 606/133 |
| 2004/0049206 | A1 * | 3/2004 | Rassman | 606/133 |

\* cited by examiner

*Primary Examiner* — Katherine Rodjom
*Assistant Examiner* — Lindsey Bachman
(74) *Attorney, Agent, or Firm* — Lawrence S. Cohen

(57) ABSTRACT

The stabilization of the dermal area around a follicular unit of hair for harvesting comprises the introduction of a small volume of fluid into the dermal area around a target follicular unit in order to stabilize the dermal area and initiate a limited time period during which the harvesting of the target follicular unit can occur.

4 Claims, 6 Drawing Sheets

HAIR HARVESTING DEVICE AND METHOD WITH LOCALIZED SUBSURFACE DERMAL FLUID INSERTION

REFERENCE TO RELATED APPLICATIONS

This application is a continuation of application Ser. No. 12/233,514 filed on Sep. 18, 2008 now U.S. Pat. No. 8,366,723 which is a continuation-in-part of application Ser. No. 11/462,102 filed on Aug. 3, 2006 the content of which are incorporated by reference herein. The present application is related to application Ser. No. 11/531,862 filed Sep. 14, 2006 the content of which is incorporated herein by reference.

BACKGROUND OF THE INVENTION

Hair transplant procedures have been carried out for decades. Initially, a punch was used to remove a circular area of hairy skin containing ten or more follicular units (of 1-4 hairs each). The area of hairy skin replaced a like area of bald skin removed from the patient. Several of such "plugs," were placed into areas in the bald part of the head.

The circular punch tool was later replaced by a hollow powered drill and the space left in the donor area was left to heal naturally. Both of these prior art procedures allowed wounds to stay open for weeks at a time exposing a patient to the discomfort from large wounds measuring 3-5 millimeters in diameter.

Today there are two standard procedures for harvesting hair, the first involves a linear incision which permits the removal of a strip of hairy skin down into the fatty level of one quarter inch and measuring a number of square inches. The resulting wound is sutured closed and the strip is dissected into grafts (under a microscope), cooled in an ice bath or refrigerator and then transplanted into a bald area in needle size holes. Forceps grasp each graft and places them into holes in the bald area. In one form for dissection the hair from the strip of scalp uses blind harvesting of grafts from the strip of hairy skin which can result in significant damage to the hair. The damage occurs because the strip of hair in the hairy skin is forced through a cutting grid in order to make grafts of a predetermined size. The cutting blades of the grid are positioned at the most ideal distance between follicles. Unfortunately, the distance between follicles varies randomly. The result is that a significant number of the hair follicles can be damaged and die.

The second harvesting technique involves the use of a microscope to dissect the hair from the excised scalp.

A third harvesting technique uses a punch which cores out from the scalp, the basic anatomical unit of hair, the follicular unit, which contains between one and four hairs each. The problems with this technique is that there can be considerable damage to the follicular unit as they are cored out from the scalp, one at a time because the skills to accomplish this are difficult to learn and master and the use of a sharp or dull punch to accomplish this runs into problems produced by the body's collagen which take on different consistencies with different people.

SUMMARY

The present invention is based on experimentation which showed that the introduction of a limited quantity of fluid in the subsurface upper papillary dermal layer not only stabilized the skin surface, but also initiated a time period during which follicular extraction can occur with extraordinarily high success rate in the harvesting of undamaged follicules.

The introduction of stabilization by near surface fluid introduction in accordance with the principles of this invention is useful along with the use of a punch and water jet scalpel disclosed in the above identified Ser. No. 11/531,862 patent application the content of which is incorporated herein by reference. The removal of the excised follicular unit may be accomplished conveniently with a suction apparatus or with a forceps which grasps the follicular unit and gently pulls it out.

Stabilization of the dermal layer around a target follicular unit is the broad concept and result of the apparatus and method of the invention. In the process of injecting a small amount of fluid into the upper papillary dermis, the fluid extends into that space and surrounds the upper part of the follicular unit when it is properly placed adjacent to the follicular unit. The fluid then moves downward into the reticular dermis. The fluid buildup is very localized to the papillary dermis and the upper part of the reticular dermis if it is kept at a small volume. The preferred range is about 0.1-1.5 ml, about 0.5 ml being preferred The hair follicular unit is surrounded by a fibrous capsule and each follicular unit (which contains between 1-4 hairs each) is surrounded by this fibrous capsule. The capsule to the follicular unit extends from the papillary dermis into the reticular dermis which contains collagen which gives the skin area strength. When the fluid is injected below the skin surface into the subsurface dermal layer outside of and around the follicular unit, the fluid extends through the papillary dermis outwardly from the point of injection and deeper into the reticular dermis. Because the follicular unit has a fibrous capsule, the capsule creates a barrier to the entry of the injection fluid which causes the capsule and the follicular unit to be compressed as the dermis is injected which, in effect, makes the capsule containing one or more hairs slightly narrower. With a narrower capsule containing the hair follicles (combined with the stabilization of the dermal space,) a situation is created that allows a mechanical punch to be slid down and around the outside of the capsule. Depending upon the thickness of the capsule which varies between different people, the barrier for the fluid to cross into the capsule varies. As more and more fluid is injected into the papillary dermis, the fluid spreads out to surround more follicular units with their capsules which will also be compressed and extracted with a mechanical punch. Some of the fluid does go deeper into the subsurface dermal layer as well as spreading outwardly in the papillary and reticular dermis. When more fluid mass is injected, the fluid that goes into the reticular dermis compresses deeper elements of the capsule of the follicular unit. If less than 1cc is injected into the papillary dermis, the stabilized area can be confined to just the area around one follicular unit.

In accordance with one embodiment of the present invention, a hollow instrument with a cutting or dissecting edge such as a drill or punch (sharp or dull) with a diameter slightly larger than a follicular unit is used to cut into the stabilized area about the follicular unit. In one iteration, the instrument includes an imaging system such as a video system which allows the health care professional to align the instrument along the axis of the follicular unit and to produce a cutting action outside of the follicular unit's critical anatomical parts and aligned properly with regard to the existing hairs (see U.S. Pat. No. 6,572,625). In all iterations of the embodiments of the present invention, the wounds are very small and this results in relatively fast healing, less bleeding and virtually no grossly visible scar tissue formation.

In one embodiment the fluid injection comprises an initial injection starting as or even slightly before the punch begins to advance into the skin. In that case the fluid is injected by a needle adjoining the punch, and extending slightly beyond the end of the punch. That initial injection will often be sufficient to stabilize the area around the follicular unit and to allow it to be extracted.

In another embodiment, fluid may, in addition to the initial injection, be further injected as the punch is advanced into the dermal layer around the follicular unit.

In one embodiment, the fluid injection needle is in fixed conjunction to the punch, so that the needle will rotate with the punch (in embodiments in which rotation is implemented). In that case the fluid injection can act as a fluid scalpel to augment the cutting by the punch.

In accordance with one embodiment a multiple dimensional stabilization gantry is employed to fix the hollow instrument and thus an imaging system for viewing a target follicular unit. Such a device can be used without direct human involvement, acquiring the appropriate orientation for follicular unit extraction based upon the same technology as described in the aforementioned patent application Ser. No. 11/531,862 and in U.S. Pat. No. 6,572,625.

In still another embodiment a suction device is positioned to capture an excised follicular unit.

DETAILED DESCRIPTION

Figure 1:
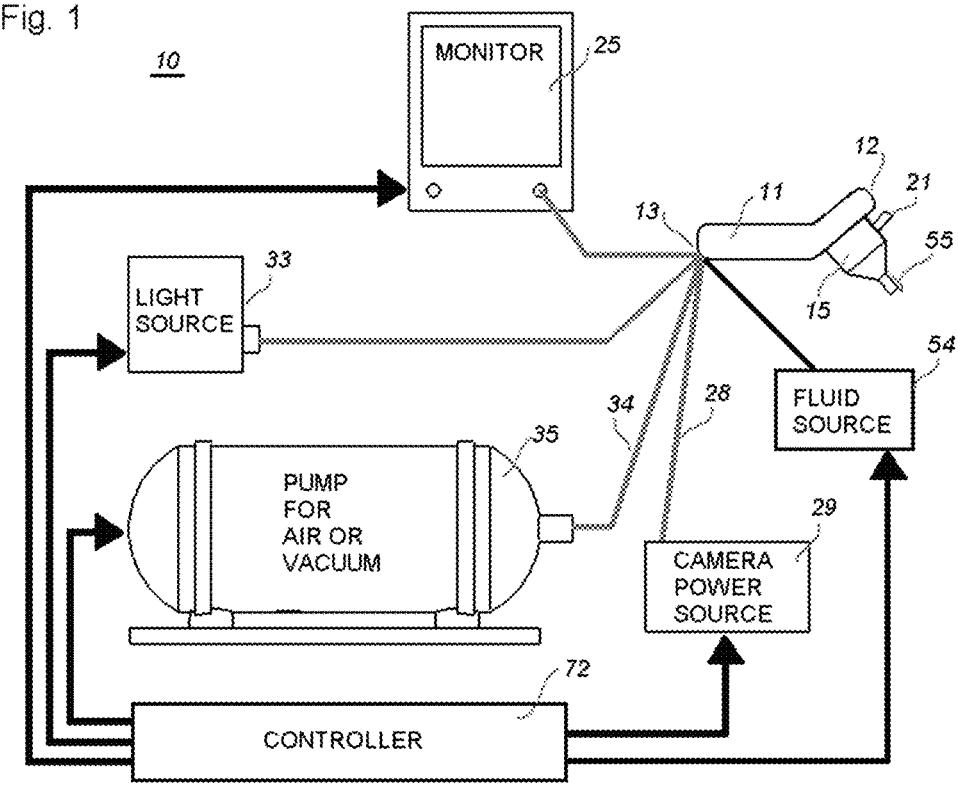
FIG. 1 is a schematic block diagram of a hair transplant harvesting device in accordance with the principles of this invention.

The following terms have the meaning given. The dermal layer and the dermis mean the layer below the epidermis and include both the papillary dermal layer and the reticular dermal layer. The term papillary dermal layer and upper papillary dermal layer are synonymous FIG. 1 is a block diagram of a system 10 in accordance with this invention. The system includes an instrument 11 having a distal end and a proximal end 12 and 13 respectively . . . . A tubular shaped subassembly 15 extends from the distal end 12 of the instrument. A controller 72 incorporates the fluid source 54, light source 33, air and vacuum pump 35, camera power source 29, and the monitor 25 for the comprehensive function of instrument 11.

Figure 2:
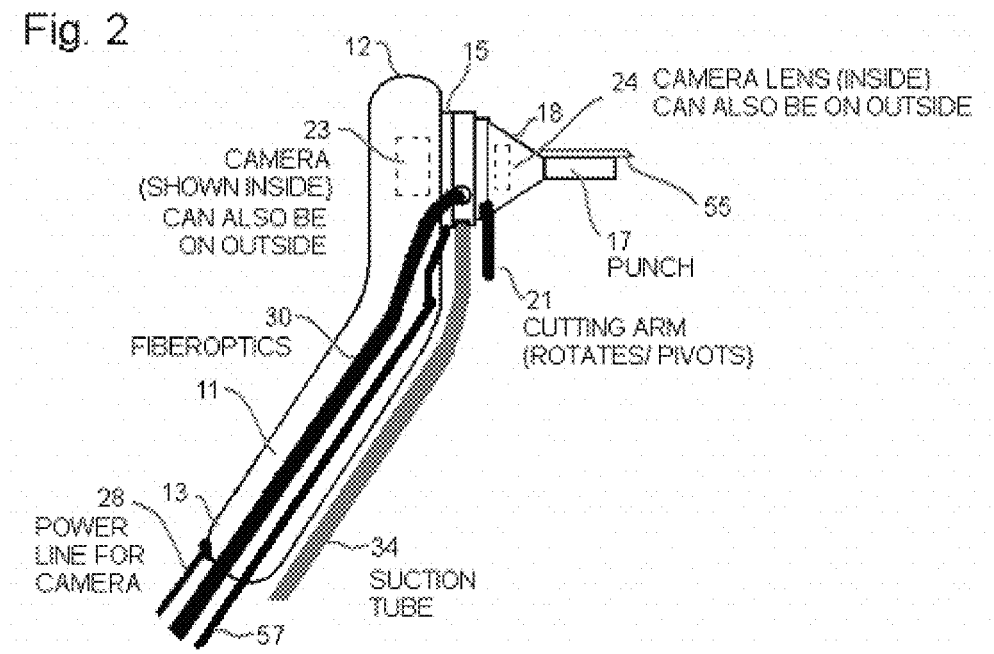
FIG. 2 is a schematic side view of a hand-held portion of the system of FIG. 1.

FIG. 2 is an enlarged schematic side view of instrument 11. Subassembly 15 can be seen to have a general shape similar to that of an instrument commonly used to examine the human ear. The subassembly includes a hollow needle or punch 17 and a conical section 18 which enlarges in diameter as it extends upwards and to the left as viewed in the figure.

Figure 3:
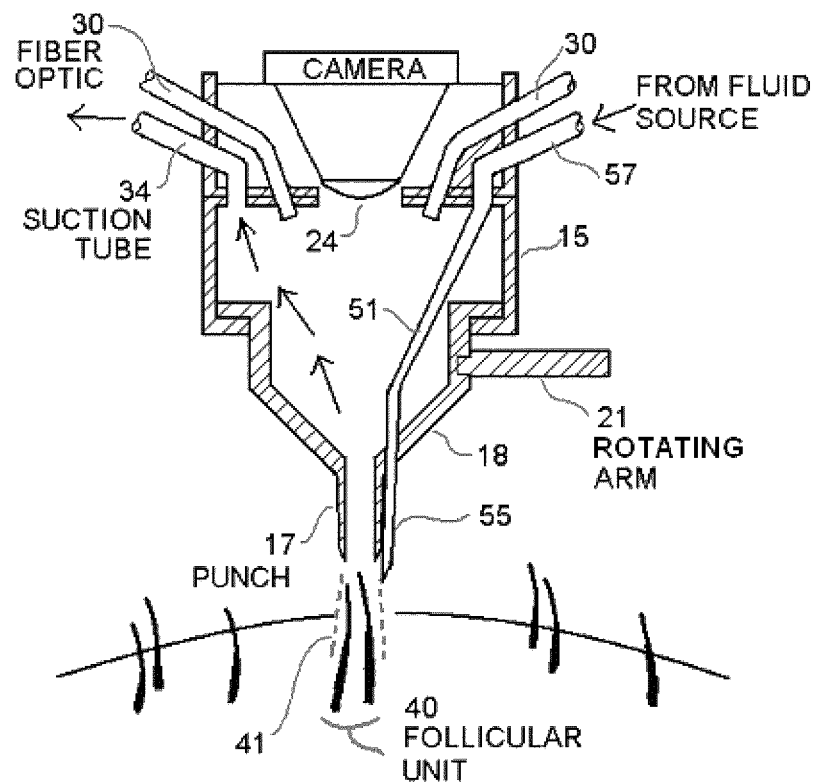
FIGS. 3 and 4 are enlarged schematic cross sectional and perspective views of a subassembly of the hand-held portion shown in FIG. 2.
Figure 4:
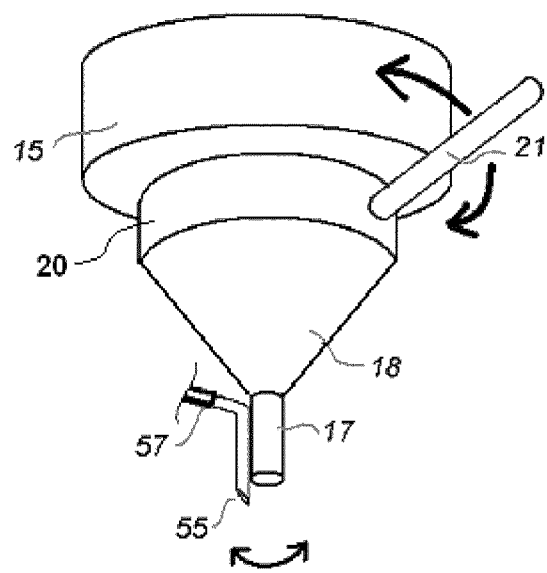

As seen in FIGS. 3 and 4, the punch 17 is formed integrally with the conical section 18 and further with the cylindrical portion 20. It will be appreciated that the apparatus can be constructed to allow the punch 17 to be replaced either as a singular unit, or by replacement of the entire conical section 18. As will be explained below, in use the punch 17 is manually advanced around the follicular unit, as shown in FIG. 2, by pushing the proximal end 12 of the instrument 11. The advancement is augmented by rotating the punch as it is advanced. Rotation is simplified by use of the rotation arm 21 and serves to rotate the punch 17 and as will be further described below, in some embodiments, the fluid injection needle 55 will also rotate. Instrument 11 includes a solid state camera such as a charge-coupled device (CCD) camera 23 represented by dashed rectangular line shown in FIG. 2. Subassembly 15 also includes a lens 24. The camera and lens are components of an imaging system positioned to capture an image viewed through the punch 17 and to display that image on monitor 25 of FIG. 1. Power for the CCD camera 23 is provided via cable 28 of FIGS. 1 and 2 from power source 29 of FIG. 1. The camera and lens components of an imaging system can also be external to the instrument 11 in an alternate configuration.

Illumination of the field of view for the camera is supplied via optical fibers 30 extending from subassembly 15 to light source 33 of FIG. 1.

In one embodiment of the invention, a suction tube 34 also is provided. Tube 34 extends between subassembly 15 and an air pump 35 shown in FIG. 1. Suction may be provided to assist in extracting a follicular unit.

For the injection of fluid, a fluid source 54 (FIG. 1) is provided. Fluid delivery tube 57 extends to needle 55 through subassembly 15 (FIG. 3) or it may be arranged outside the subassembly (FIG. 2). The needle 55 is adjacent to punch 17.

FIG. 3 shows an enlarged cross section of subassembly 15 showing the relative positions of lens 24, optical fibers 30, suction tube 34, punch 17, rotating conical section 18, fluid delivery tube 57 connected to fluid injection needle 55, and rotation arm 21. Rotation arm 21 is an optional component that facilitates the use of the instrument 11 by rotating the punch as it advances. Other means to facilitate rotation can be employed such as simply manually rotating the cylindrical portion 20, which could be knurled or covered with a plastic/rubber grip. Alternatively, the punch can be advanced without rotation. The rotation can also be automated with a motor.

FIG. 4 shows an enlarged perspective view of subassembly 15 showing punch 17, conical section 18, and cutting arm 21. It is clear from the views of FIGS. 3 and 4 that a user observes a follicular unit 40 as shown in FIG. 3 by moving instrument 11 (FIG. 1) until a selected follicular unit is in the center of the field of view 41. In another embodiment of the invention the alignment of the field of view can be offset whereas the camera 23 and lens 24 system can be external to the subassembly 15 to compensate the correct alignment through computation from controller 72. The user observes the field of view in monitor 25 of FIG. 1. The diameter of punch 17 is chosen sufficiently wide to cut past beyond the critical anatomical structures of a follicular unit thus avoiding any damage to the unit. The diameter of punch 17 should be in the range of about 0.5 mm to 1.5 mm, preferably about 0.9 mm. The punch distal end is preferably somewhat sharpened and preferably is serrated.

As described above, it is important in accordance with the principles of this invention, that the fluid injection needle 55 is positioned in alignment with the punch 17 such that it extends beyond the distal end of the punch 17 a distance to ensure that the distal end of the needle 55 extends into the upper part of the dermal layer adjacent a target follicular unit such that a fluid (preferably a physiologic saline solution) is introduced directly into the dermal layer. The needle 55 preferably extends in parallel axial alignment with the punch 17 and should be as close as possible to it so that the fluid will effect stabilization of the dermal area around the target follicular unit. In one embodiment the needle 55 can be affixed to the side of the punch 17. More generally the needle 55 can be affixed to move with rotation as well as advancement of the punch 17.

Figure 5:
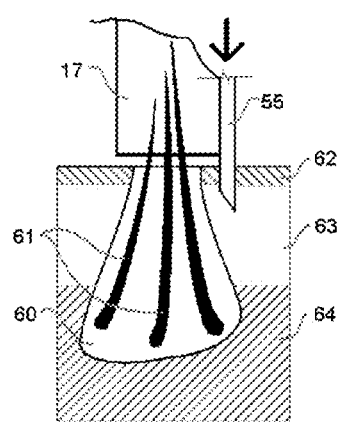
FIGS. 5 and 6A and 6B are representations of a representative target follicular unit illustrating fluid placement for stabilization.
Figure 6A:
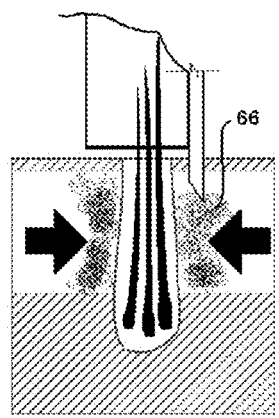
Figure 6B:
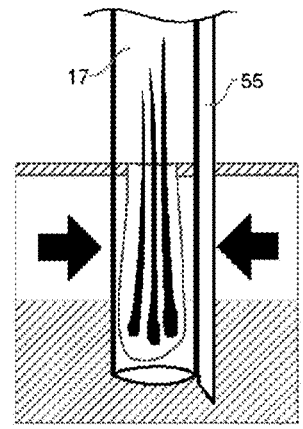

FIGS. 3 and 5 illustrate the distance that the needle 55 extends beyond the punch 17; a distance of about one to two millimeters. This distance is important in that the fluid must be injected into upper (papillary) dermal layer before the punch 17 cuts into that layer. Specifically, FIG. 5 shows a representative follicular unit with bulb 60 and hairs 61. The figure also represents a cross section through the scalp of a patient illustrating the epidermal (surface) layer 62, papillary dermal layer 63 and reticular layer 64 FIG. 6A also shows the micro tumescence 66 in the dermal layer. It has been found that by inserting fluid directly into the upper (papillary) dermal area, reliable stabilization of the dermal area around a target follicular unit is achieved for a limited time determined by the speed at which the fluid is absorbed. This time is measured in seconds for fluid to be absorbed (as short as one to ten seconds) during which time the punch 17 is advanced into the scalp to a position below bulb 60 as shown in FIG. 6B. During advancement of the punch 17, additional fluid may be injected through needle 55 and even at the final position of punch 17, additional fluid may be introduced. A comparison of FIGS. 5 and 6A makes clear the compression of a follicular unit outer root sheath (the Trichelemma) caused by the fluid. It is the basic concept that injection of the fluid be sufficiently in advance of the punch through the upper (papillary) dermal layer that the stabilization be achieved. While this does not have exact relationships of the timing, it is preferred that the injection of the fluid be substantially complete as the punch 17 enters the upper (papillary) dermal layer. Also, in the alternative embodiment, injection of fluid will continue as the punch is advanced, and the fluid may also be injected into the fatty layer (reticular layer). In one implementation, the fluid will also flow around the bottom of the follicular unit, but that may not occur consistently, and is not considered essential. In that regard, the process should be completed by the extraction step as soon as the punch has reached its furthest travel. Notably, in the preferred embodiment, as the punch is rotated the fluid injection needle 55 also rotates which enhances distribution of the fluid around the follicular capsule and also acts to assist in the manner of a scalpel to free the follicular unit.

Figure 7A:
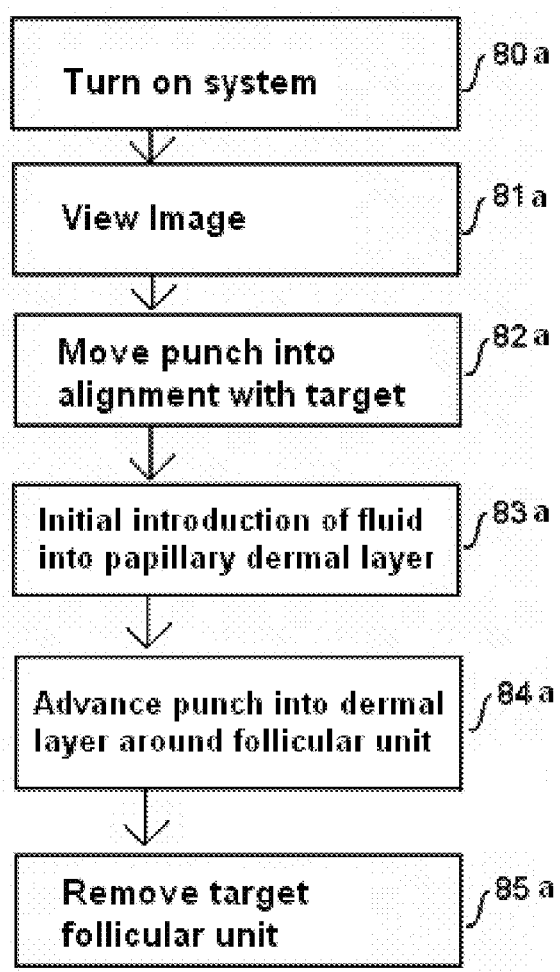
FIG. 7a is a flow diagram of one embodiment of the method practiced by the system of FIGS. 1-4.

FIG. 7a is a flow diagram of the method practiced by the system of FIG. 1 in the embodiment in which fluid is injected only just as the punch advancement begins, including just before advancement begins. The system and method is preceded by the patient's hair being cut to a short length so that the donor area of the head exhibits erect hair follicles. A user positions the hollow needle over the skin of a patient after turning on the monitor, the light source and the camera. The procedure starts by turning on the system as represented by block 80a of FIG. 7a and the image of the field of view is observed on the monitor 25 as indicated by block 81a.

The user moves the instrument 11 until the field of view through the punch 17 is in alignment with a follicular unit producing an image. This step is represented by block 82a.

The instrument is now properly positioned with the top of the punch 17 juxtaposed against the skin of a patient with a selected follicular unit in the field of view and with the axis of the punch 17 aligned with the axis of the follicular unit and due to its extended length beyond the end of the punch 17, into the upper dermal layer. The user now administers a small amount of fluid, typically a saline solution or Ringer's solution or other physiological solution through the needle 55, step 83a in FIG. 7a which will enter into the upper dermal layer it. The amount of fluid can be as low as about 0.1 milliliters and up to about 1.5 ml, about 0.5 ml being preferred. The fluid is introduced at a high pressure to overcome the resistance of the injection needle and the papillary dermal tissue. A pressure of about 600 to 1200 psi may be needed to overcome this resistance. The introduction of the fluid stabilizes the dermal layer surrounding the target follicular unit and initiates a time period during which target extraction is accomplished with an extraordinarily high success rate in harvesting undamaged follicular units. The time period is based on absorption of the fluid which reverses the stabilization. Typically, the initial introduction of fluid, prior to beginning the advancement of the punch will be on the order of 1-3 seconds. Then the advancement of the punch will take about 1-2 seconds. The total process can be completed in as little as 5 seconds, especially if suction is used for the extraction step. Once the dermal layer is stabilized in this manner, target excise and extraction is carried out by advancing a punch into the stabilized dermis about the target as shown in block 84a of FIG. 7a.

Figure 7B:
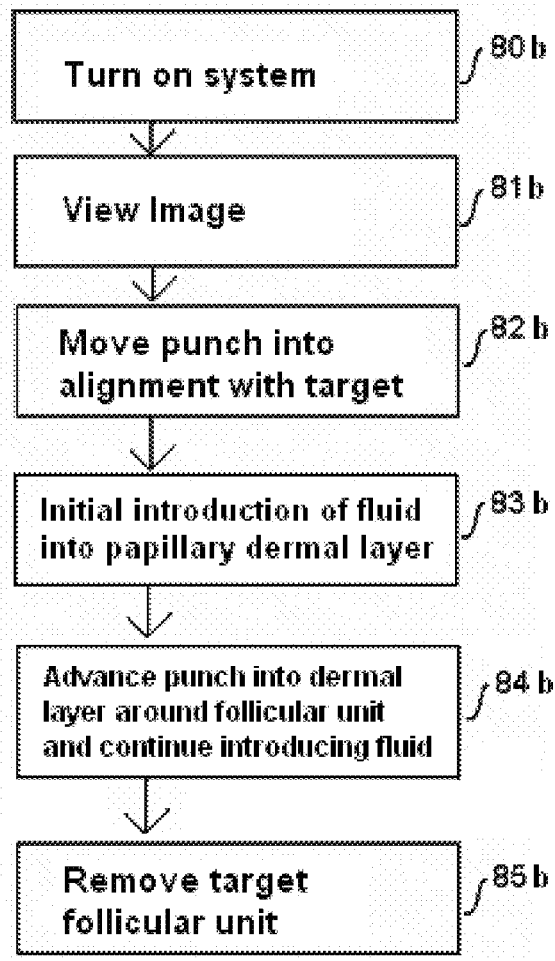
FIG. 7b is a flow diagram of another embodiment of the method of the invention.

In the alternative embodiment shown in FIG. 7b, as the punch 17, and with it the needle 55 are advanced as shown in block 84b, fluid injection beyond the initial injection (as in 83a) in is continued. The target follicular unit can be conveniently captured via a suction apparatus or a grabbing instrument such as a forceps as shown in block 85a of FIG. 7a. The common steps of FIGS. 7a and 7b are as described above, the difference residing in the continuation of fluid injection in step 84b The various steps of the excising procedure herein occurs optimally within a time window of less than 5 seconds once the limited amounts of fluid is introduced into the dermal layer at a target.

The removal of the excised follicular unit is expedited by the suction tube 34 and vacuum pump 35 of FIG. 1. But any suitable method of removal is adequate. Tweezers may be used, for example.

The spacing between adjacent follicular units varies randomly but typically it is approximately one millimeter. The critical anatomical structure of a unit is only a fraction of that distance thus dictating a minimum diameter of about 0.50 millimeters for the hollow cutting elements of the punch. It is thus, convenient to secure an x/y/z gantry (such as shown in FIG. 8) to the head of a patient and to secure the "hand held" instrument so that it can be controlled by adjusting micromanipulators.

Figure 8:
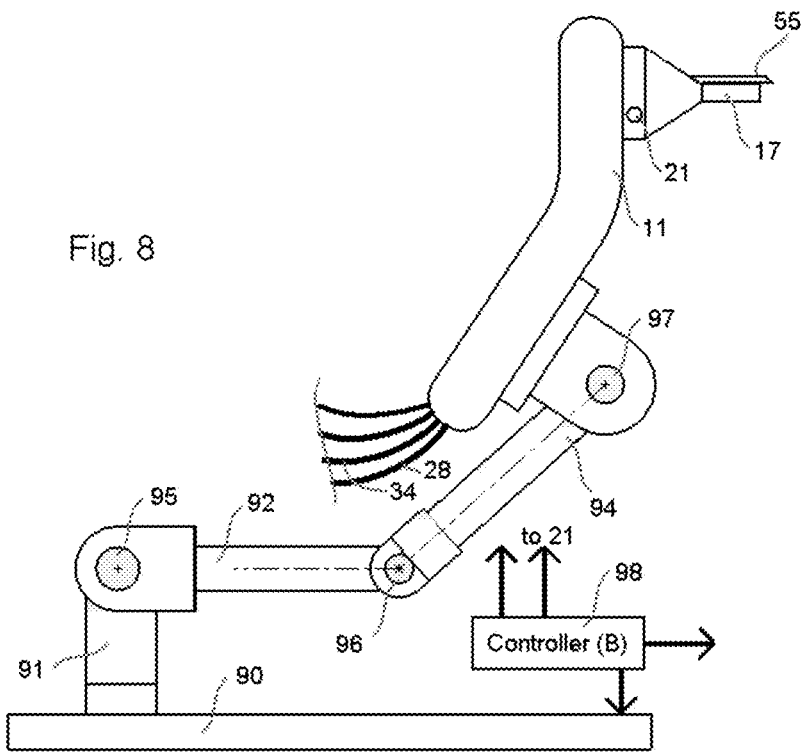
FIG. 8 is a schematic side view of a robotic subassembly for excising follicular units from a donor area.

FIG. 8 is a schematic side view of a robotic assembly for extracting follicular units of hair from a donor area in the manner described above. The robotic assembly comprises a positioning table 90 to which the instrument 11 of FIGS. 1, 2 and 3 is connected by means of post 91. Positioning table 90 is operative to move post 91 in x, y, z and rotational planes. Post 91 is operative to actuate arm 92 along and or around its axis. Instrument 11 is connected to post 91 by arms 92 and 94 at pivot points 95, 96 and 97 which are set to adjust punch 17 with a selected donor area.

The operation is controlled by a controller 98 operative to move punch 17 to a position shown in FIG. 5 to introduce fluid via needle 55 of FIG. 5 into the dermal layer at a target and to initiate a time during which the punch is advanced along its axis to a depth to excise or extract the follicular unit and/or to manipulate rotating arm 21 to facilitate the removal of the follicular unit. Needle 55 at the depth shown in FIG. 6b also can facilitate the removal of the follicular unit by a small injection of the fluid effectively severing micro fibrils at the base of the follicular unit.

Figure 9:
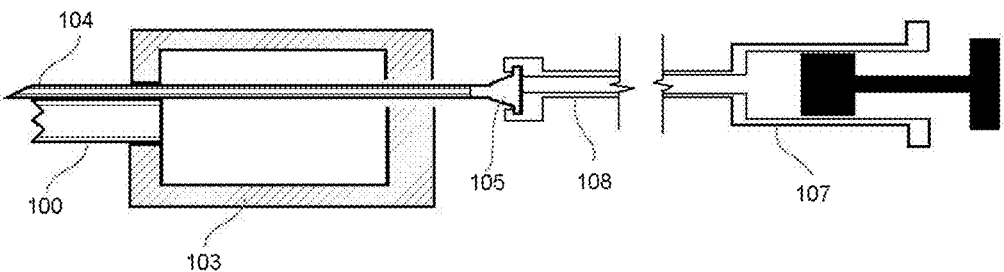
FIG. 9 is a schematic illustration of a hand held embodiment in accordance with the principles of this invention.
Figure 10:
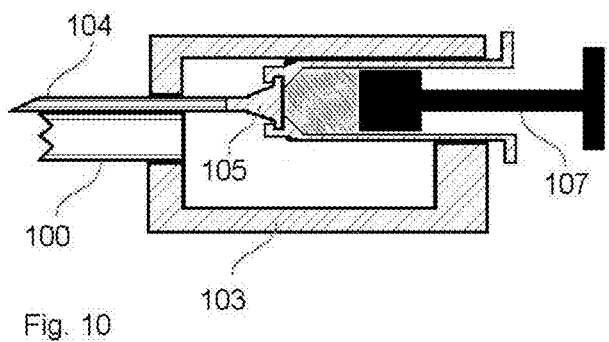
FIG. 10 is a schematic illustration of a hand held embodiment in accordance with the principle of this invention.

FIGS. 9 and 10 show alternative embodiments where a syringe is positioned by hand without the aid of a camera and monitor as in FIG. 1 or a robotic assembly as shown in FIG. 8. In hand held embodiments the punch and the auxiliary fluid injection needle are affixed to one another such that the distal end of the auxiliary needle is properly positioned in the dermal layer when the punch abuts the skin surface. FIG. 9 shows the punch 100 as part of a punch body 103 which serves as a handle for a user. The proximal end of the needle extends beyond the punch body to the right as viewed in the figure.

In practice, a syringe 107 is connected to the proximal end of the auxiliary needle either directly or via suitable tubing 108 as shown. The syringe conveniently is prepackaged or preprogrammed to contain approximately 0.1 ml of fluid for introducing the micro-tumescence into the upper papillary dermal layer thus stabilizing a target follicular unit.

If a larger amount of fluid is introduced, it will extend along the dermal layer even to adjacent follicular units. The adjacent unit could be harvested also as long as it is excised within the narrow window available before the fluid is absorbed. This is the case with all embodiments in this description.

FIG. 10 shows an embodiment where the proximal end 105 of the auxiliary needle is located within the punch body rather than extending beyond the punch body as shown in FIG. 9. In the embodiment of FIG. 10, the syringe is inserted into the punch body where it couples to the auxiliary needle. In either case (FIG. 9 or 10), the rotation of the punch is optional as is the choice to inject fluid only initially as in step 83a or further injection as in step 84b. The distal end of the punch is serrated as shown to facilitate the excising of a target. Rather than a serrated end, a sharp or semi-sharp punch can be used.

In summary, in accordance with the principles of this invention, an instrument for excising a follicular unit comprises a hollow punch with an auxiliary hollow needle which extends beyond the distal end of the hollow punch a distance to position the distal end of the auxiliary needle into the dermal layer of a target when the distal end of the punch impacts the scalp surface. When the instrument is so positioned, a limited quantity of fluid under high pressure is inserted into the papillary dermal area initiating the excising operation to be completed by the time the fluid is absorbed. As the punch is advanced, the injection of fluid can be continued.

The excise operation can be carried out by advancing the punch with or without rotation. The excising operation (and follicular unit capture) has to occur prior to the absorption of the fluid in the dermal layer for the extraordinary success rate of harvesting of undamaged units to be achieved. It is to be understood that the positioning of the auxiliary hollow needle with respect to the punch and the short time for extraction suggests that a robotic instrumentation is preferable, although operation manually is possible by highly trained and skillful operators.

It is to be understood that the description herein is merely illustrative of the principles of this invention and that various changes and modifications thereof may be made by those skilled in the art within the spirit and scope of the invention as encompassed by the claims below. For example, the invention has been described in terms of a fluid delivering hollow needle extending from and attached to a coring device, the punch. It is possible, however, to employ a hollow needle, unattached to a coring device, so long as the user us sufficiently skilled to deliver the fluid to the dermal layer with sufficient precision to stabilize the target follicular unit. An annular ring or geometric change in the fluid injection needle geometry could provide a 'stop' for proper positioning the needle tip when the stop abuts the skin surface.

The foregoing Detailed Description of exemplary and preferred embodiments is presented for purposes of illustration and disclosure in accordance with the requirements of the law. It is not intended to be exhaustive nor to limit the invention to the precise form or forms described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. This disclosure has been made with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising step(s) for . . . ".

What is claimed is:

1. A method for extraction of a target follicular unit for the purpose of implantation comprising:
    providing a fluid conduit with a distal end for discharging fluid and a punch with a distal end, the fluid conduit being in parallel axial alignment with and extending a distance of about one to two millimeters beyond the distal end of the punch and an apparatus for advancing each of them and a source of fluid for injection through the fluid conduit;
    causing stabilization of the dermal area around a target follicular unit and causing the target follicular unit to compress by injecting fluid from the fluid conduit into the dermal layer proximate to the target follicular unit whereby the fluid will extend around the target follicular unit;
    advancing the punch around the target follicular unit in the said dermal layer to a final position in which the target follicular unit has been excised;
    said injection of fluid commencing as or slightly before the punch begins to advance into the skin;
    extracting the target follicular unit.

2. The method of claim 1 further comprising applying suction to the target follicular unit as part of extracting the target follicular unit.

3. The method of claim 1 wherein the punch has a diameter selected to cut beyond critical anatomical structures of the target follicular unit thereby to avoid any damage to the target follicular unit.

4. The method of claim 3 wherein the diameter of the punch is in the range of about 0.5 mm to 1.5 mm.

* * * * *